US012570772B2

(12) United States Patent
Reesink et al.

(10) Patent No.: US 12,570,772 B2
(45) Date of Patent: Mar. 10, 2026

(54) PROCESS FOR THE HYDROGENATION OF HYDROCARBON RESINS USING CATALYSTS WITH PROTECTIVE COATINGS

(71) Applicant: BASF Corporation, Florham Park, NJ (US)

(72) Inventors: Bernard Reesink, De Meern (NL); Robert Terorde, De Meern (NL); Irina Yarulina, De Meern (NL); Robert Willem Gosselink, Antwerp (BE)

(73) Assignee: IQATALYST B.V., De Meern (NL)

( * ) Notice: Subject to any disclaimer, the term of this patent is extended or adjusted under 35 U.S.C. 154(b) by 424 days.

(21) Appl. No.: 17/795,302

(22) PCT Filed: Feb. 15, 2021

(86) PCT No.: PCT/EP2021/053625
§ 371 (c)(1),
(2) Date: Jul. 26, 2022

(87) PCT Pub. No.: WO2021/160879
PCT Pub. Date: Aug. 19, 2021

(65) Prior Publication Data

US 2023/0082782 A1     Mar. 16, 2023

(30) Foreign Application Priority Data

Feb. 14, 2020   (EP) .................................... 20157416

(51) Int. Cl.
*C08F 8/04*       (2006.01)
*B01J 23/755*     (2006.01)
*C07C 5/02*       (2006.01)

(52) U.S. Cl.
CPC ............... *C08F 8/04* (2013.01); *B01J 23/755* (2013.01); *C07C 5/02* (2013.01)

(58) Field of Classification Search
CPC . B01J 33/00; B01J 35/63; B01J 35/633; B01J 35/635; B01J 35/638; B01J 2231/60; B01J 2231/64; B01J 2231/645; B01J 2231/646; C08F 8/04
See application file for complete search history.

(56) References Cited

U.S. PATENT DOCUMENTS

| | | | | |
|---|---|---|---|---|
| 4,980,327 A | * | 12/1990 | Wolfe .................... | B01J 23/755 502/167 |
| 5,681,787 A | | 10/1997 | Seamans | |
| 6,294,498 B1 | * | 9/2001 | Darcissac .............. | B01J 23/888 502/402 |
| 9,045,410 B2 | * | 6/2015 | Bouwman ............... | C07C 51/36 |
| 2005/0027136 A1 | * | 2/2005 | Toor ......................... | A23D 9/00 554/141 |
| 2006/0100452 A1 | * | 5/2006 | Berben .................... | B01J 35/77 502/252 |
| 2008/0161588 A1 | | 7/2008 | Hassan et al. | |
| 2014/0256972 A1 | | 9/2014 | Bouwman et al. | |
| 2014/0336287 A1 | * | 11/2014 | Terorde .................. | C10G 2/334 502/159 |

FOREIGN PATENT DOCUMENTS

| | | | |
|---|---|---|---|
| EP | 3865558 A1 | | 8/2021 |
| GB | 2246083 | * | 1/1992 |
| KR | 1020090094401 A | | 9/2009 |
| WO | 2004035204 A1 | | 4/2004 |
| WO | 2015008247 A2 | | 1/2015 |
| WO | 2017208164 A1 | | 12/2017 |

OTHER PUBLICATIONS

International Preliminary Report on Patentability for International application No. PCT/EP2021/053625, mailed Feb. 23, 2022, 7 pages.
Rejection Decision with English translation for Chinese Patent Application No. 202180014385.5 dated May 10, 2025.
Shu et al., "Science and Technology of Biodiesel Fuel", Metallurgical Industry Press 2012, 8 pages.
Office Action with English Translation for Indian Patent Application No. 202227046647 dated Nopvember 11, 2025, 15 pages.
Office Action with English translation for Korean Patent Application No. 10-2022-7031392 dated Dec. 22, 2025, 17 pages.

* cited by examiner

*Primary Examiner* — Robert C Boyle
(74) *Attorney, Agent, or Firm* — Lowenstein Sandler LLP

(57)                ABSTRACT

The present invention relates to a process for the hydrogenation of an unsaturated hydrocarbon feedstock comprising: (1) preparing a granular material, wherein the particles of the granular material comprise a hydrogenation catalyst, or a precursor thereof, and one or more organic compounds, wherein the one or more organic compounds comprise one or more carboxlic acid and/or one or more ester and/or one or more ether moieties; (2) providing an unsaturated hydrocarbon feedstock; (3) preparing a mixture comprising the granular material obtained in (1), the unsaturated hydrocarbon feedstock provided in (2), hydrogen gas, and optionally a solvent system; (4) heating the mixture prepared in (3) to a temperature in the range of from 210 to 360° C. for hydrogenating the hydrocarbon feedstock.

15 Claims, 2 Drawing Sheets

PROCESS FOR THE HYDROGENATION OF HYDROCARBON RESINS USING CATALYSTS WITH PROTECTIVE COATINGS

TECHNICAL FIELD

The present invention relates to a process for the hydrogenation of an unsaturated hydrocarbon feedstock.

INTRODUCTION

The market for hydrogenated petroleum resins, used as adhesives in for example packaging and nonwovens, is booming. Hydrogenation of these resins improves the thermal stability and produces a desired water white product. WO 2015/008247 A2 for example relates to a Ni/Si/Al mixed oxide and to its use for the hydrogenation of hydrocarbon resins.

Currently the resin hydrogenation Ni powder catalysts are produced by precipitation, reduction and stabilization. There are, however, drawbacks associated with the production process of this type of catalysts. The risk of dust formation, especially of carcinogenic, mutagenic and reprotoxic substances (in this case Ni), is of high concern, especially with regulations getting stricter over time. Additionally, due to the pyrophoric nature of this material, extra caution must be taken upon exposure to air, which in this case is accounted for by a lengthy and therefore costly stabilization step is needed. Coating the reduced Ni with a compatible medium can overcome these drawbacks. This medium should, however, be invisible to the resin feed. As such, the material should be highly similar or even identical to the respective resin.

Thus, polystyrene, with a molecular weight of ~2800 g/mol, is for example chemically highly similar to a C9 hydrocarbon resin feed. In this regard, WO 2017/208164 A1 relates to metal catalysts protected with coating of molten polymer and their use in the hydrogenation of hydrocarbon resin feedstocks. Similarly, such coating of reduced Ni is performed with fats and oils for providing the protected catalyst as droplets for use in the hydrogenation of oleochemical feedstocks such as vegetable oil. Thus, WO 2004/035204 A1 relates to Ni/Si/Al mixed oxides coated with hardened soybean fat as a protective coating which then dissolves in the feedstock of unsaturated fatty compounds. U.S. Pat. No. 9,045,410 B2, on the other hand, relates to Ni supported on silica as catalyst for the hydrogenation of unsaturated fatty materials, wherein the catalyst may be coated in a fatty substance (e.g. hardened soy bean or palm oil fat), such that the catalyst is suspended in droplets forming a protective layer.

US 2008/161588 A1 relates to a method for hydrogenating fat or oil using nickel silicate catalyst. The catalyst is supplied as solid "droplets" that are coated with a protective hydrogenated vegetable oil that has been hydrogenated to a point where the material is solid at room temperature and soy bean oil is used as the feedstock.

US 2005/027136 A1 relates to a method of hydrogenating an unsaturated feedstock using a nickel on an alumina support catalyst dispersed in the fat component that is solid at room temperature.

US 2014/336287 A1 relates to hydrogenation of unsaturated fats, oils and/or hydrocarbon resins using a coated nickel catalyst in the form of granules. The nickel catalyst may be coated with C10-C13 aliphatic hydrocarbon liquids, hydrodesulfurized heavy naphtha, white spirits, and tetralin, aromatics, ester, and ethers.

There remains, however, a need for the provision of new methods of protecting hydrogenation catalysts for use in the hydrogenation of resin feedstocks, and in particular of resin feedstocks which are either liquid at room temperature or have a low melting or softening point such that they may not be used per se as the protective material. In particular, there remains a need for the provision of methods for protecting hydrogenation catalysts for use in the hydrogenation of liquid resin feedstocks or resin feedstocks with a low melting or softening point which are more time- and/or cost-efficient and/or which are more environmentally friendly than those known in the art.

DETAILED DESCRIPTION

It was the object of the present invention to provide an alternative method of protecting a hydrogenation catalyst for use in the hydrogenation of a hydrocarbon resin feedstock which is more time- and cost-efficient. In particular, it was the object of the present invention to provide a method for protecting a hydrogenation catalyst for use in the hydrogenation of a hydrocarbon resin feedstock which involves the use of readily available and in particular the use of natural products or derivatives thereof. Thus, it has surprisingly been found that a hydrogenation catalyst for the hydrogenation of hydrocarbon feedstocks may be effectively protected by coating thereof with one or more organic compounds containing one or more carboxylic acid and/or one or more ester moieties, wherein said compounds are deoxygenated in situ under the conditions for the hydrogenation of hydrocarbon feedstocks, as a result of which they are transformed to water, CO, and/or $CO_2$ and hydrocarbons. In fact, this is quite unexpected in view of the technical prejudice of the art, wherein protective coatings of hardened vegetable oil or fat would lead to a contamination of the hydrogenated hydrocarbon end product, if it were to be used in the method for the hydrogenation of hydrocarbon feedstocks (see e.g. WO 2017/208164 A1: page 2, first full paragraph). As a result, it has quite unexpectedly been found that a protective coating containing compounds comprising one or more carboxylic acid and/or one or more ester moieties and in particular protective coatings comprising natural fats may be employed for the hydrogenation of hydrocarbon feedstocks without contaminating the hydrocarbon feedstock, but rather affording at most hydrocarbons which may easily be separated from the hydrogenated hydrocarbon product by distillation or the like.

Therefore, the present invention relates to a process for the hydrogenation of an unsaturated hydrocarbon feedstock comprising:

(1) preparing a granular material, wherein the particles of the granular material comprise a hydrogenation catalyst, or a precursor thereof, and one or more organic compounds, wherein the one or more organic compounds comprise one or more carboxylic acid and/or one or more ester and/or one or more ether moieties, preferably one or more carboxylic acid and/or one or more ester moieties, and more preferably one or more ester moieties;

(2) providing an unsaturated hydrocarbon feedstock;

(3) preparing a mixture comprising the granular material obtained in (1), the unsaturated hydrocarbon feedstock provided in (2), hydrogen gas, and optionally a solvent system;

(4) heating the mixture prepared in (3) to a temperature in the range of from 210 to 360° C. for hydrogenating the hydrocarbon feedstock, preferably in the range of from 220 to 340° C., more preferably of from 230 to 320° C., more preferably of from 240 to 300° C., more preferably of from 250 to 290° C., more preferably of from 260 to 280° C., and more preferably of from 265 to 275° C.

The process may comprise further process steps. Also, any one of the defined process steps may comprise further process steps, in particular relative to the preparation of a granular material. It is preferred that for preparing the granular material in (1) the process comprises:

(1. a) providing a hydrogenation catalyst or a precursor thereof;

(1. b) providing one or more organic compounds comprising one or more carboxylic acid and/or one or more ester and/or one or more ether moieties, preferably one or more carboxylic acid and/or one or more ester moieties, and more preferably one or more ester moieties;

(1. c) optionally heating the one or more organic compounds provided in (1. b) to a temperature above the melting point of the one or more organic compounds;

(1. d) dispersing the hydrogenation catalyst provided in (1. a) in the one or more organic compounds provided in (1. b) and optionally heated in (1. c);

(1. e) shaping the dispersion obtained in (1. d), preferably into particles.

(1. f.) cooling the shaped dispersion obtained in (1. e) to a temperature below the melting point of the one or more organic compounds;

It is preferred that in (1) the one or more organic compounds comprise one or more alkyl moieties, more preferably one or more C10-C24 alkyl moieties, more preferably one or more C12-C22 alkyl moieties, more preferably one or more C14-C20 alkyl moieties, and more preferably one or more C16-C18 alkyl moieties.

It is preferred that in (1) the one or more organic compounds comprise one or more alkylene moieties, more preferably one or more C1-C6 alkylene moieties, more preferably one or more C2-C4 alkylene moieties, and more preferably one or more C3 alkylene moieties.

It is preferred that in (1) the one or more organic compounds comprise one or more compounds selected from the group consisting of triglycerides, fatty acids, and mixtures of two or more thereof, preferably from the group consisting of vegetable oils and mixtures of two or more thereof, more preferably from the group consisting of palm oil, soybean oil, rapeseed oil, sunflower seed oil, peanut oil, cottonseed oil, palm kernel oil, coconut oil, olive oil, and mixtures of two or more thereof, more preferably from the group consisting of palm oil, soybean oil, cottonseed oil, and mixtures of two or more thereof, more preferably from the group consisting of palm oil, soybean oil, and mixtures of two or more thereof, wherein more preferably the one or more organic compounds comprise palm and/or soybean oil, preferably palm oil, wherein more preferably the one or more organic compounds consist of palm and/or soybean oil, preferably palm oil.

In the case where in (1) the one or more organic compounds comprise triglycerides and/or fatty acids, it is preferred that the triglycerides and/or fatty acids are hydrogenated triglycerides and/or fatty acids.

It is preferred that in (1) the one or more organic compounds comprise one or more ether moieties, more preferably two or more ether moieties, and one or more alkylene moieties, preferably two or more alkylene moieties, more preferably two or more C1-C3 alkylene moieties, more preferably two or more C1-C2 alkylene moieties, and more preferably two or more C1 alkylene moieties, wherein more preferably the one or more organic compounds comprise one or more polyoxoalkylenes, more preferably one or more polyoxo(C1-C3)alkylenes, more preferably one or more polyoxo(C1-C2)alkylenes, more preferably one or more polyoxo(C1)alkylenes, wherein more preferably the one or more organic compounds comprise polyoxomethylene.

It is preferred that in (1) the melting point of the one or more organic compounds is in the range of from 30 to 100° C., more preferably from 35 to 90° C., more preferably from 40 to 80° C., more preferably from 45 to 75° C., more preferably from 50 to 70° C., more preferably from 55 to 65° C.

It is preferred that the unsaturated hydrocarbon feedstock comprises one or more alkanes, more preferably one or more C5 to C17 alkanes, more preferably one or more C5 to C15 alkanes, more preferably one or more C5 to C13 alkanes, more preferably one or more C5 to C11 alkanes, more preferably one or more C5 to C9 alkanes, more preferably one or more C5 and/or C9 alkanes, and more preferably one or more C9 alkanes.

It is preferred that the unsaturated hydrocarbon feedstock comprises one or more compounds selected from the group consisting of C5 resins, C9 resins, C5/C9 copolymer resins, dicyclopentadiene resins, and mixtures of two or more thereof, more preferably from the group consisting of C5 resins, C9 resins, C5/C9 copolymer resins, and mixtures of two or more thereof, more preferably from the group consisting of C5 resins, C9 resins, and mixtures of two or more thereof, wherein more preferably the unsaturated hydrocarbon feedstock comprises C9 resins, wherein more preferably, the hydrocarbon feedstock consists of C5 and/or C9 resins, preferably of C9 resins.

It is preferred that the unsaturated hydrocarbon feedstock contains 800 wppm or less of sulfur, calculated as the element, more preferably from 500 wppm or less, more preferably 300 wppm or less, more preferably 250 wppm or less, more preferably 200 wppm or less, more preferably 180 wppm or less, more preferably 150 wppm or less, more preferably 130 wppm or less, more preferably 100 wppm or less, more preferably 80 wppm or less, more preferably 60 wppm or less, more preferably 40 wppm or less, more preferably 20 wppm or less, more preferably 10 wppm or less, and more preferably 5 wppm or less.

It is preferred that the solvent system comprises one or more hydrocarbons, more preferably one or more alkanes, more preferably one or more C5-C18 alkanes, more preferably one or more C5-C16 alkanes, more preferably one or more C5-C14 alkanes, more preferably one or more C6-C13 alkanes, more preferably one or more C7-C12 alkanes, more preferably one or more C8-C11 alkanes, and more preferably one or more C9-C10 alkanes.

It is preferred that the weight ratio of the hydrogenation catalyst to the one or more organic compounds in the particles of the granular material in (1) is in the range of from 5:95 to 75:25, more preferably from 10:90 to 60:40, more preferably from 15:85 to 50:50, more preferably from 20:80 to 45:55, more preferably from 23:77 to 40:60, more preferably from 25:75 to 34:66, and more preferably from 27:73 to 32:68.

It is preferred that the hydrogenation catalyst in (1) comprises Ni, wherein preferably the amount of Ni in the hydrogenation catalyst is in the range of from 5 to 95 weight-% calculated as the element and based on 100 weight-% of the hydrogenation catalyst, preferably of from 10 to 90 weight-%, more preferably from 20 to 80 weight-%, more preferably from 30 to 70 weight-%, more preferably from 35 to 65 weight-%, more preferably from 40 to 60 weight-%, and more preferably from 45 to 55 weight-%.

In the case where the hydrogenation catalyst in (1) comprises Ni, it is preferred that Ni is present in the elemental form, preferably in an amount in the range of from 10 to 99 weight-% based on 100 weight-% of Ni contained in the hydrogenation catalyst calculated as the element, preferably in an amount in the range of from 30 to 98 weight-%, more preferably from 50 to 95 weight-%, more preferably from 60 to 90 weight-%, more preferably from 70 to 85 weight-%, more preferably from 75 to 82 weight-%, and more preferably from 78 to 80 weight-%.

Further, it is preferred that the hydrogenation catalyst in (1) comprises one or more transition metals selected from the group consisting of Rh, Ir, Ru, Pt, Pd, and combinations of two or more thereof, wherein more preferably the hydrogenation catalyst in (1) comprises Pt and/or Pd, more preferably Pt.

In the case where the hydrogenation catalyst comprises the one or more transition metals selected from the group consisting of Rh, Ir, Ru, Pt, Pd, and combinations of two or more thereof, it is preferred that the amount of the one or more transition metals in the hydrogenation catalyst is in the range of from 0.01 to 10 weight-% calculated as the element and based on 100 weight-% of the hydrogenation catalyst, more preferably of from 0.05 to 7 weight-%, more preferably from 0.1 to 5 weight-%, more preferably from 0.5 to 3 weight-%, more preferably from 0.7 to 2 weight-%, more preferably from 0.8 to 1.5 weight-%, and more preferably from 0.9 to 1 weight-%.

Further in the case where the hydrogenation catalyst in (1) comprises the one or more transition metals selected from the group consisting of Rh, Ir, Ru, Pt, Pd, and combinations of two or more thereof, it is preferred that the one or more transition metals are present in the elemental form in an amount of 50 weight-% or more based on 100 weight-% of the one or more transition metals calculated as the element, more preferably in an amount of 80 weight-% or more, more preferably of 90 weight-% or more, more preferably of 95 weight-% or more, more preferably of 98 weight-% or more, more preferably of 99 weight-% or more, and more preferably of 99.9 weight-% or more.

It is preferred that the hydrogenation catalyst in (1) comprises one or more oxides selected from the group consisting of refractory metal oxides and mixtures thereof, more preferably from the group consisting of silica, alumina, magnesia, and mixtures of two or more thereof, wherein more preferably the hydrogenation catalyst comprises silica and/or alumina, preferably silica or silica and alumina, and more preferably silica.

In the case where the hydrogenation catalyst in (1) comprises one or more oxides selected from the group consisting of refractory metal oxides and mixtures thereof, it is preferred that the amount of the one or more oxides in the hydrogenation catalyst is in the range of from 5 to 95 weight-% calculated as the oxide and based on 100 weight-% of the hydrogenation catalyst, more preferably of from 8 to 90 weight-%, more preferably from 10 to 80 weight-%, more preferably from 13 to 70 weight-%, more preferably from 15 to 65 weight-%, more preferably from 18 to 60 weight-%, and more preferably from 20 to 55 weight-%.

According to the present invention it is preferred that the hydrogenation catalyst further comprises a component capable of trapping sulfides for preventing the poisoning of the catalytically active components in the hydrogenation catalyst, especially in particular and preferred embodiments thereof comprising one or more transition metals selected from the group consisting of Rh, Ir, Ru, Pt, Pd, and combinations of two or more thereof, and in particular in particular and preferred embodiments comprising Pt and/or Pd, in particular Pt. Thus, in this respect, it is preferred that the hydrogenation catalyst in (1) further comprises one or metal oxides selected from the group consisting of oxides of silver, lanthanum, antimony, nickel, bismuth, cadmium, lead, tin, vanadium, calcium, strontium, barium, cobalt, copper, tungsten, zinc, molybdenum, manganese, and iron, including mixed oxides of two or more thereof, wherein preferably the hydrogenation catalyst in (1) further comprises a metal oxide of zinc and/or iron, preferably zinc oxide.

It is preferred that the pore volume of the hydrogenation catalyst in (1) is in the range of from 0.1 to 1.5 ml/g, wherein the pore volume refers to the hydrogenation catalyst devoid of any compounds in its pores, more preferably from 0.2 to 1.2 ml/g, more preferably from 0.3 to 1 ml/g, more preferably from 0.4 to 0.8 ml/g, more preferably from 0.5 to 0.7 ml/g, and more preferably from 0.55 to 0.6 ml/g, wherein the pore volume is preferably determined according to ISO 15901-3: 2007.

It is preferred that the average pore diameter of the hydrogenation catalyst in (1) is in the range of from 10 to 500 Å, wherein the average pore diameter in particular refers to the hydrogenation catalyst devoid of any compounds in its pores, more preferably from 30 to 400 Å, more preferably from 50 to 300 Å, more preferably from 60 to 250 Å, more preferably from 70 to 200 Å, more preferably from 80 to 150 Å, more preferably from 90 to 120 Å, and more preferably from 95 to 105 Å, wherein the average pore diameter is preferably determined according to ISO 15901-1: 2016.

It is preferred that the BET surface area of the hydrogenation catalyst in (1) is in the range of from 100 to 600 m²/g, wherein the BET surface area in particular refers to the hydrogenation catalyst devoid of any compounds in its pores, more preferably from 120 to 500 m²/g, more preferably from 140 to 450 m²/g, more preferably from 160 to 400 m²/g, more preferably from 180 to 350 m²/g, more preferably from 200 to 300 m²/g, more preferably from 220 to 280 m²/g, and more preferably from 240 to 260 m²/g, wherein the BET surface area is preferably determined according to ISO 9277: 2010.

It is preferred that the average particle size D50 by volume of the hydrogenation catalyst is in the range of from 1 to 50 μm, more preferably from 3 to 25 μm, more preferably from 4 to 15 μm, more preferably from 5 to 10 μm, more preferably from 6 to 8 μm, and more preferably from 6.5 to 7 μm, wherein the average particle size D50 by volume is preferably determined according to ISO 13320: 2009.

It is preferred that the weight ratio of the granular material to the unsaturated hydrocarbon feedstock in the mixture in (3) is in the range of from 1:99 to 40:60, more preferably from 3:97 to 35:65, more preferably from 5:95 to 30:70, more preferably from 7:93 to 25:75, more preferably from 9:91 to 23:77, more preferably from 11:89 to 21:79, more preferably from 13:87 to 19:81, and more preferably from 15:85 to 17:83.

It is preferred that the weight ratio of the unsaturated hydrocarbon feedstock to the solvent system in the mixture in (3) is in the range of from 5:95 to 95:5, more preferably from 10:90 to 90:10, more preferably from 20:80 to 80:20, more preferably from 25:75 to 75:25, more preferably from 30:70 to 70:30, more preferably from 35:65 to 65:35, more preferably from 40:60 to 60:40, and more preferably from 45:55 to 55:45.

It is preferred that (4) is conducted at a pressure in the range of from 10 to 250 bar, more preferably from 20 to 200 bar, more preferably from 30 to 180 bar, more preferably from 40 to 150 bar, more preferably from 50 to 120 bar, more preferably from 60 to 100 bar, more preferably from 70 to 90 bar, and more preferably from 75 to 85 bar.

In the case where (4) is conducted at a pressure in the range of from 10 to 120 bar, it is preferred that the gas phase of the mixture prepared in (3) and heated in (4) comprises 50 volume-% or more of hydrogen gas, more preferably 80 volume-% or more, more preferably 90 volume-% or more, more preferably 95 volume-% or more, more preferably 98 volume-% or more, more preferably 99 volume-% or more, and more preferably 99.9 volume-% or more.

It is preferred that (4) is conducted for a duration in the range of from 0.1 h to 20 h, more preferably of from 0.25 h to 10 h, more preferably of from 0.5 h to 5 h, more preferably of from 1 h to 3 h, and more preferably of from 1.5 h to 2.5 h.

As disclosed above, the process may comprise further process steps. Also, any one of the defined process steps may comprise further process steps, in particular relative to the preparation of a hydrogenation catalyst.

According to a first alternative, it is preferred that for providing the hydrogenation catalyst precursor in (1) the process comprises:

(i) providing an aqueous solution comprising one or more salts of one or more transition metals;

(ii) providing an aqueous solution comprising one or more bases;

(iii) providing an aqueous dispersion comprising one or more refractory metal oxides in water;

(iv) adding the aqueous solution provided in (i) and the aqueous solution provided in (ii) to the aqueous dispersion provided in (iii) for precipitating a hydrogenation catalyst precursor;

(v) isolating the hydrogenation catalyst precursor obtained in (iv); and (vi) optionally washing and/or drying and/or calcining the hydrogenation catalyst precursor isolated in (v).

It is preferred that the hydrogenation catalyst in (1) is prepared by a process according to the first alternative comprising (i), (ii), (iii), (iv), (v), and (vi), as disclosed above, wherein the process further comprises:

(vii) reducing the hydrogenation catalyst precursor obtained in (v) or (vi) in a hydrogen atmosphere for obtaining a hydrogenation catalyst.

It is preferred that the hydrogenation catalyst in (1) is prepared by a process according to the first alternative comprising (i), (ii), (iii), (iv), (v), (vi), and (vii), as disclosed above, wherein the process further comprises:

(viii) passivating the hydrogenation catalyst obtained in (vii) in an atmosphere comprising air, preferably in an atmosphere consisting of air.

In the case where the process further comprises (i) according to the first alternative as disclosed above, it is preferred that in (i) the one or more transition metals are selected from the group consisting of Ni, Rh, Ir, Ru, Pt, Pd, and combinations of two or more thereof, more preferably from the group consisting of Ni, Pt, Pd and combinations of two or more thereof, wherein more preferably the one or more transition metals comprise Ni and/or Pt, preferably Ni, wherein more preferably the one or more transition metals are Ni and/or Pt, preferably Ni.

In the case where the process further comprises (ii) according to the first alternative as disclosed above, it is preferred that in (ii) the one or more bases comprise one or more compounds selected from the group consisting of inorganic and organic bases, more preferably from the group of inorganic bases, wherein preferably the one or more bases are selected from the group consisting of hydroxides, carbonates, aluminates, and mixtures of two or more thereof, more preferably from the group consisting of alkali metal hydroxides, alkali metal carbonates, alkali metal aluminates, and mixtures of two or more thereof, more preferably from the group consisting of alkali metal carbonates, alkali metal aluminates, and mixtures of two or more thereof, wherein more preferably the one or more bases comprise one or more alkali metal carbonates, wherein the alkali metal is preferably selected from the group consisting of Li, Na, K, Rb, Cs, and mixtures of two or more thereof, more preferably from the group consisting of Li, Na, K, and mixtures of two or more thereof, wherein more preferably the alkali metal is Na and/or K, preferably Na.

In the case where the process further comprises (iii) according to the first alternative as disclosed above, it is preferred that in (iii) the one or more refractory metal oxides are selected from the group consisting of silica, alumina, magnesia, and mixtures of two or more thereof, wherein more preferably the one or more refractory metal oxides comprise silica and/or alumina, preferably silica or silica and alumina, and more preferably silica, wherein more preferably the one or more refractory metal oxides consist of silica and/or alumina, preferably of silica or of silica and alumina, and more preferably of silica.

Further in the case where the process further comprises (iii) according to the first alternative as disclosed above, it is preferred that in (iii) the one or more refractory metal oxides have a pore volume in the range of from 0.3 to 5 ml/g, more preferably of from 0.5 to 4 ml/g, more preferably of from 0.8 to 3.5 ml/g, more preferably of from 1 to 3 ml/g, more preferably of from 1.3 to 2.5 ml/g, more preferably of from 1.5 to 2 ml/g, more preferably of from 1.6 to 1.8 ml/g, and more preferably of from 1.7 to 1.75 ml/g, wherein the pore volume is preferably determined according to ISO 15901-3: 2007.

In the case where the process further comprises (i), (ii), (iii), and (iv) according to the first alternative as disclosed above, it is preferred that in (iv) the addition of the aqueous solution provided in (i) and the aqueous solution provided in (ii) to the aqueous dispersion provided in (iii) is conducted subsequently or simultaneously, preferably simultaneously.

Further in the case where the process further comprises (i), (ii), (iii), and (iv) according to the first alternative as disclosed above, it is preferred that (iv) is conducted at a temperature in the range of from 25 to 95° C., more preferably of from 30 to 90° C., more preferably of from 35 to 85° C., more preferably of from 40 to 80° C., more preferably of from 45 to 75° C., more preferably of from 50 to 70° C., and more preferably of from 55 to 65° C.

Further in the case where the process further comprises (i), (ii), (iii), and (iv) according to the first alternative as disclosed above, it is preferred that in (iv) the pH is maintained in the range of from 5 to 10 during the precipitation of the mixed oxide, more preferably of from 5.5 to 9.5, more preferably of from 6 to 9, more preferably of from 6.5 to 8.5, and more preferably of from 7 to 8.

In the case where the process further comprises (vii), it is preferred that reduction in (vii) according to the first alternative as disclosed above, is conducted at a temperature in the range of from 200 to 500° C., more preferably from 250 to 470° C., more preferably from 300 to 440° C., more preferably from 350 to 420° C., and more preferably from 380 to 400° C.

In the case where the process further comprises reduction in (vii) according to the first alternative as disclosed above, it is preferred that reduction in (vii) is conducted for a duration in the range of from 0.25 to 5 h, more preferably from 0.5 to 4 h, more preferably from 1 to 3.5 h, more preferably from 1.25 to 3 h, more preferably from 1.5 to 2.5 h, and more preferably from 1.75 to 2.25 h.

In the case where the process further comprises passivation in (viii) according to the first alternative as disclosed above, it is preferred that passivation in (viii) is conducted at a temperature in the range of from 75 to 150° C., more preferably from 80 to 130° C., more preferably from 85 to 120° C., more preferably from 90 to 110° C., and more preferably from 95 to 105° C.

In the case where the process further comprises passivation in (viii) according to the first alternative as disclosed above, it is preferred that passivation in (viii) is conducted for a duration in the range of from 0.25 to 4 h, more preferably from 0.5 to 3 h, more preferably from 0.75 to 2.5 h, more preferably from 1 to 2 h, and more preferably from 1.25 to 1.75 h.

According to a second alternative, it is preferred that for providing the hydrogenation catalyst in (1), the process comprises:

(i) providing an aqueous solution comprising one or more salts of one or more transition metals;

(ii) providing an aqueous solution comprising one or more precursor salts of silica;

(iii) providing an aqueous solution comprising one or more precursor salts of alumina;

(iv) adding the aqueous solution provided in (i) and the aqueous solution provided in (ii) to the aqueous solution provided in (iii) for precipitating hydrogenation catalyst precursor;

(v) isolating the hydrogenation catalyst precursor obtained in (iv);

(vi) optionally washing and/or drying and/or calcining the hydrogenation catalyst precursor isolated in (v).

It is preferred that the hydrogenation catalyst in (1) is prepared by a process according to the second alternative comprising (i), (ii), (iii), (iv), (v), and (vi), as disclosed above, wherein the process further comprises:

(vii) reducing the hydrogenation catalyst precursor obtained in (v) or (vi) in a hydrogen atmosphere for obtaining a hydrogenation catalyst.

It is preferred that the hydrogenation catalyst in (1) is prepared by a process according to the second alternative comprising (i), (ii), (iii), (iv), (v), (vi), and (vii), as disclosed above, wherein the process further comprises:

(viii) passivating the hydrogenation catalyst obtained in (vii) in an atmosphere comprising air, preferably in an atmosphere consisting of air.

In the case where the process further comprises (i) according to the second alternative as disclosed above, it is preferred that in (i) the one or more transition metals are selected from the group consisting of Ni, Rh, Ir, Ru, Pt, Pd, and combinations of two or more thereof, more preferably from the group consisting of Ni, Pt, Pd and combinations of two or more thereof, wherein more preferably the one or more transition metals comprise Ni and/or Pt, preferably Ni, wherein more preferably the one or more transition metals are Ni and/or Pt, preferably Ni.

In the case where the process further comprises (i), (ii), (iii), and (iv) according to the second alternative as disclosed above, it is preferred that in (iv) the addition of the aqueous solution provided in (i) and the aqueous solution provided in (ii) to the aqueous solution provided in (iii) is conducted subsequently or simultaneously, preferably simultaneously.

In the case where the process further comprises (iv) according to the second alternative as disclosed above, it is preferred that (iv) is conducted at a temperature in the range of from 35 to 100° C., more preferably from 50 to 99° C., more preferably from 70 to 98° C., more preferably from 80 to 97° C., more preferably from 85 to 96° C., and more preferably from 90 to 95° C.

Further in the case where the process further comprises (iv) according to the second alternative as disclosed above, it is preferred that in (iv) the pH is maintained in the range of from 6 to 10 during the precipitation of the mixed oxide, more preferably of from 6.5 to 9.5, more preferably of from 7 to 9, and more preferably of from 7.5 to 8.5.

In the case where the process further comprises (vi) according to the second alternative as disclosed above, it is preferred that calcining in (vi) is conducted at a temperature in the range of from 200 to 700° C., more preferably from 250 to 600° C., more preferably from 300 to 500° C., more preferably from 325 to 450° C., and more preferably from 350 to 400° C.

In the case where the process further comprises (vii) according to the second alternative as disclosed above, it is preferred that reduction in (vii) is conducted at a temperature in the range of from 200 to 500° C., more preferably from 300 to 470° C., more preferably from 350 to 450° C., more preferably from 400 to 440° C., and more preferably from 420 to 430° C.

In the case where the process further comprises (vii) according to the second alternative as disclosed above, it is preferred that reduction in (vii) is conducted for a duration in the range of from 0.25 to 5 h, more preferably from 0.5 to 4 h, more preferably from 1 to 3.5 h, more preferably from 1.25 to 3 h, more preferably from 1.5 to 2.5 h, and more preferably from 1.75 to 2.25 h.

In the case where the process further comprises (viii) according to the second alternative as disclosed above, it is preferred that passivation in (viii) is conducted at a temperature in the range of from 75 to 150° C., more preferably from 80 to 130° C., more preferably from 85 to 120° C., more preferably from 90 to 110° C., and more preferably from 95 to 105° C.

In the case where the process further comprises (viii) according to the second alternative as disclosed above, it is preferred that passivation in (viii) is conducted for a duration in the range of from 0.25 to 4 h, more preferably from 0.5 to 3 h, more preferably from 0.75 to 2.5 h, more preferably from 1 to 2 h, and more preferably from 1.25 to 1.75 h.

It is preferred that the granular material is in the form of pastilles, flakes or droplets.

It is preferred that the granular materials displays an average particle size in the range of from 1 to 25 mm, more preferably from 2 to 15 mm, more preferably from 3 to 10 mm, more preferably from 4 to 8 mm, and more preferably from 5 to 6 mm.

The unit bar(abs) refers to an absolute pressure of $10^5$ Pa and the unit Angstrom refers to a length of $10^{-10}$ m.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4". Further, it is explicitly noted that the following set of embodiments is not the set of claims determining the extent of protection, but represents a suitably structured part of the description directed to general and preferred aspects of the present invention.

1. Process for the hydrogenation of an unsaturated hydrocarbon feedstock comprising:
   (1) preparing a granular material, wherein the particles of the granular material comprise a hydrogenation catalyst, or a precursor thereof, and one or more organic compounds, wherein the one or more organic compounds comprise one or more carboxylic acid and/or one or more ester and/or one or more ether moieties, preferably one or more carboxylic acid and/or one or more ester moieties, and more preferably one or more ester moieties;
   (2) providing an unsaturated hydrocarbon feedstock;
   (3) preparing a mixture comprising the granular material obtained in (1), the unsaturated hydrocarbon feedstock provided in (2), hydrogen gas, and optionally a solvent system;
   (4) heating the mixture prepared in (3) to a temperature in the range of from 210 to 360° C. for hydrogenating the hydrocarbon feedstock, preferably in the range of from 220 to 340° C., more preferably of from 230 to 320° C., more preferably of from 240 to 300° C., more preferably of from 250 to 290° C., more preferably of from 260 to 280° C., and more preferably of from 265 to 275° C.

2. The process of embodiment 1, wherein for preparing the granular material in (1), the process comprises:
   (1. a) providing a hydrogenation catalyst or a precursor thereof;
   (1. b) providing one or more organic compounds comprising one or more carboxylic acid and/or one or more ester and/or one or more ether moieties, preferably one or more carboxylic acid and/or one or more ester moieties, and more preferably one or more ester moieties;
   (1. c) optionally heating the one or more organic compounds provided in (1. b) to a temperature above the melting point of the one or more organic compounds;
   (1. d) dispersing the hydrogenation catalyst provided in (1. a) in the one or more organic compounds provided in (1. b) and optionally heated in (1. c);
   (1. e) shaping the dispersion obtained in (1. d), preferably into particles;
   (1. f.) cooling the shaped dispersion obtained in (1. e) to a temperature below the melting point of the one or more organic compounds.

3. The process of embodiment 1 or 2, wherein in (1) the one or more organic compounds comprise one or more alkyl moieties, preferably one or more C10-C24 alkyl moieties, more preferably one or more C12-C22 alkyl moieties, more preferably one or more C14-C20 alkyl moieties, and more preferably one or more C16-C18 alkyl moieties.

4. The process of any one of embodiments 1 to 3, wherein in (1) the one or more organic compounds comprise one or more alkylene moieties, preferably one or more C1-C6 alkylene moieties, more preferably one or more C2-C4 alkylene moieties, and more preferably one or more C3 alkylene moieties.

5. The process of any one of embodiments 1 to 4, wherein in (1) the one or more organic compounds comprise one or more compounds selected from the group consisting of triglycerides, fatty acids, and mixtures of two or more thereof, preferably from the group consisting of vegetable oils and mixtures of two or more thereof, more preferably from the group consisting of palm oil, soybean oil, rapeseed oil, sunflower seed oil, peanut oil, cottonseed oil, palm kernel oil, coconut oil, olive oil, and mixtures of two or more thereof, more preferably from the group consisting of palm oil, soybean oil, cottonseed oil, and mixtures of two or more thereof, more preferably from the group consisting of palm oil, soybean oil, and mixtures of two or more thereof, wherein more preferably the one or more organic compounds comprise palm and/or soybean oil, preferably palm oil, wherein more preferably the one or more organic compounds consist of palm and/or soybean oil, preferably palm oil.

6. The process of embodiment 5, wherein the triglycerides and/or fatty acids are hydrogenated triglycerides and/or fatty acids.

7. The process of any one of embodiments 1 to 6, wherein in (1) the one or more organic compounds comprise one or more ether moieties, preferably two or more ether moieties, and one or more alkylene moieties, preferably two or more alkylene moieties, more preferably two or more C1-C3 alkylene moieties, more preferably two or more C1-C2 alkylene moieties, and more preferably two or more C1 alkylene moieties, wherein more preferably the one or more organic compounds comprise one or more polyoxoalkylenes, more preferably one or more polyoxo(C1-C3)alkylenes, more preferably one or more polyoxo(C1-C2)alkylenes, more preferably one or more polyoxo(C1)alkylenes, wherein more preferably the one or more organic compounds comprise polyoxomethylene.

8. The process of any one of embodiments 1 to 7, wherein in (1) the melting point of the one or more organic compounds is in the range of from 30 to 100° C., preferably from 35 to 90° C., more preferably from 40 to 80° C., more preferably from 45 to 75° C., more preferably from 50 to 70° C., and more preferably from 55 to 65° C.

9. The process of any one of embodiments 1 to 8, wherein the unsaturated hydrocarbon feedstock comprises one or more alkanes, preferably one or more C5 to C17 alkanes, more preferably one or more C5 to C15 alkanes, more preferably one or more C5 to C13 alkanes, more preferably one or more C5 to C11 alkanes, more preferably one or more C5 to C9 alkanes, more preferably one or more C5 and/or C9 alkanes, and more preferably one or more C9 alkanes.

10. The process of any one of embodiments 1 to 9, wherein the unsaturated hydrocarbon feedstock comprises one or more compounds selected from the group consisting of C5 resins, C9 resins, C5/C9 copolymer resins, dicyclopentadiene resins, and mixtures of two or more thereof, preferably from the group consisting of C5 resins, C9 resins, C5/C9 copolymer resins, and mixtures of two or more thereof, more preferably from the group consisting of C5 resins, C9 resins, and mixtures of two or more thereof, wherein more preferably the unsaturated hydrocarbon feedstock comprises C9 resins, wherein more preferably, the hydrocarbon feedstock consists of C5 and/or C9 resins, preferably of C9 resins.

11. The process of any one of embodiments 1 to 10, wherein the unsaturated hydrocarbon feedstock contains 800 wppm or less of sulfur calculated as the element, preferably 500 wppm or less, more preferably 300 wppm or less, more preferably 250 wppm or less, more preferably 200 wppm or less, more preferably 180 wppm or less, more preferably 150 wppm or less, more preferably 130 wppm or less, 100 wppm or less, more preferably 80 wppm or less, more preferably 60 wppm or less, more preferably 40 wppm or less, more preferably 20 wppm or less, more preferably 10 wppm or less, and more preferably 5 wppm or less.

12. The process of any one of embodiments 1 to 11, wherein the solvent system comprises one or more hydrocarbons, preferably one or more alkanes, more preferably one or more C5-C18 alkanes, more preferably one or more C5-C16 alkanes, more preferably one or more C5-C14 alkanes, more preferably one or more C6-C13 alkanes, more preferably one or more C7-C12 alkanes, more preferably one or more C8-C11 alkanes, and more preferably one or more C9-C10 alkanes.

13. The process of any one of embodiments 1 to 12, wherein the weight ratio of the hydrogenation catalyst to the one or more organic compounds in the particles of the granular material in (1) is in the range of from 5:95 to 75:25, preferably from 10:90 to 60:40, more preferably from 15:85 to 50:50, more preferably from 20:80 to 45:55, more preferably from 23:77 to 40:60, more preferably from 25:75 to 34:66, and more preferably from 27:73 to 32:68.

14. The process of any one of embodiments 1 to 13, wherein the hydrogenation catalyst in (1) comprises Ni, wherein preferably the amount of Ni in the hydrogenation catalyst is in the range of from 5 to 95 weight-% calculated as the element and based on 100 weight-% of the hydrogenation catalyst, preferably of from 10 to 90 weight-%, more preferably from 20 to 80 weight-%, more preferably from 30 to 70 weight-%, more preferably from 35 to 65 weight-%, more preferably from 40 to 60 weight-%, and more preferably from 45 to 55 weight-%.

15. The process of embodiment 14, wherein Ni is present in the elemental form in an amount in the range of from 10 to 99 weight-% based on 100 weight-% of Ni contained in the hydrogenation catalyst calculated as the element, preferably in an amount in the range of from 30 to 98 weight-%, more preferably from 50 to 95 weight-%, more preferably from 60 to 90 weight-%, more preferably from 70 to 85 weight-%, more preferably from 75 to 82 weight-%, and more preferably from 78 to 80 weight-%.

16. The process of any one of embodiments 1 to 15, wherein the hydrogenation catalyst in (1) comprises one or more transition metals selected from the group consisting of Rh, Ir, Ru, Pt, Pd, and combinations of two or more thereof, wherein preferably the hydrogenation catalyst in (1) comprises Pt and/or Pd, preferably Pt.

17. The process of embodiment 16, wherein the amount of the one or more transition metals in the hydrogenation catalyst is in the range of from 0.01 to 10 weight-% calculated as the element and based on 100 weight-% of the hydrogenation catalyst, preferably of from 0.05 to 7 weight-%, more preferably from 0.1 to 5 weight-%, more preferably from 0.5 to 3 weight-%, more preferably from 0.7 to 2 weight-%, more preferably from 0.8 to 1.5 weight-%, and more preferably from 0.9 to 1 weight-%.

18. The process of embodiment 16 or 17, wherein the one or more transition metals are present in the elemental form in an amount of 50 weight-% or more based on 100 weight-% of the one or more transition metals calculated as the element, preferably in an amount of 80 weight-% or more, more preferably of 90 weight-% or more, more preferably of 95 weight-% or more, more preferably of 98 weight-% or more, more preferably of 99 weight-% or more, and more preferably of 99.9 weight-% or more.

19. The process of any one of embodiments 1 to 18, wherein the hydrogenation catalyst in (1) comprises one or more oxides selected from the group consisting of refractory metal oxides and mixtures thereof, preferably from the group consisting of silica, alumina, magnesia, and mixtures of two or more thereof, wherein more preferably the hydrogenation catalyst comprises silica and/or alumina, preferably silica or silica and alumina, and more preferably silica.

20. The process of embodiment 19, wherein the amount of the one or more oxides in the hydrogenation catalyst is in the range of from 5 to 95 weight-% calculated as the oxide and based on 100 weight-% of the hydrogenation catalyst, preferably of from 8 to 90 weight-%, more preferably from 10 to 80 weight-%, more preferably from 13 to 70 weight-%, more preferably from 15 to 65 weight-%, more preferably from 18 to 60 weight-%, and more preferably from 20 to 55 weight-%.

21. The process of any one of embodiments 1 to 20, wherein the hydrogenation catalyst in (1) further comprises one or metal oxides selected from the group consisting of oxides of silver, lanthanum, antimony, nickel, bismuth, cadmium, lead, tin, vanadium, calcium, strontium, barium, cobalt, copper, tungsten, zinc, molybdenum, manganese, and iron, including mixed oxides of two or more thereof, wherein preferably the hydrogenation catalyst in (1) further comprises a metal oxide of zinc and/or iron, preferably zinc oxide.

22. The process of any one of embodiments 1 to 21, wherein the pore volume of the hydrogenation catalyst in (1) is in the range of from 0.1 to 1.5 ml/g, wherein the pore volume refers to the hydrogenation catalyst devoid of any compounds in its pores, preferably from 0.2 to 1.2 ml/g, more preferably from 0.3 to 1 ml/g, more preferably from 0.4 to 0.8 ml/g, more preferably from 0.5 to 0.7 ml/g, and more preferably from 0.55 to 0.6 ml/g, wherein the pore volume is preferably determined according to ISO 15901-3: 2007.

23. The process of any one of embodiments 1 to 22, wherein the average pore diameter of the hydrogenation catalyst in (1) is in the range of from 10 to 500 Å, wherein the average pore diameter refers to the hydrogenation catalyst devoid of any compounds in its pores, preferably from 30 to 400 Å, more preferably from 50 to 300 Å, more preferably from 60 to 250 Å, more preferably from 70 to 200 Å, more preferably from 80 to 150 Å, more preferably from 90 to 120 Å, and more preferably from 95 to 105 Å, wherein the average pore diameter is preferably determined according to ISO 15901-1: 2016.

24. The process of any one of embodiments 1 to 23, wherein the BET surface area of the hydrogenation catalyst in (1) is in the range of from 100 to 600 m²/g, wherein the BET surface area refers to the hydrogenation catalyst devoid of any compounds in its pores, more preferably from 120 to 500 m$^2$/g, more preferably from 140 to 450 m$^2$/g, more preferably from 160 to 400 m$^2$/g, more preferably from 180 to 350 m$^2$/g, more preferably from 200 to 300 m$^2$/g, more preferably from 220 to 280 m$^2$/g, and more preferably from 240 to 260 m$^2$/g, wherein the BET surface area is preferably determined according to ISO 9277: 2010.

25. The process of any one of embodiments 1 to 24, wherein the average particle size D50 by volume of the hydrogenation catalyst is in the range of from 1 to 50 μm, preferably from 3 to 25 μm, more preferably from 4 to 15 μm, more preferably from 5 to 10 μm, more preferably from 6 to 8 μm, and more preferably from 6.5 to 7 μm, wherein the average particle size D50 by volume is preferably determined according to ISO 13320: 2009.

26. The process of any one of embodiments 1 to 25, wherein the weight ratio of the granular material to the unsaturated hydrocarbon feedstock in the mixture in (3) is in the range of from 1:99 to 40:60, preferably from 3:97 to 35:65, more preferably from 5:95 to 30:70, more preferably from 7:93 to 25:75, more preferably from 9:91 to 23:77, more preferably from 11:89 to 21:79, more preferably from 13:87 to 19:81, and more preferably from 15:85 to 17:83.

27. The process of any one of embodiments 1 to 26, wherein the weight ratio of the unsaturated hydrocarbon feedstock to the solvent system in the mixture in (3) is in the range of from 5:95 to 95:5, preferably from 10:90 to 90:10, more preferably from 20:80 to 80:20, more preferably from 25:75 to 75:25, more preferably from 30:70 to 70:30, more preferably from 35:65 to 65:35, more preferably from 40:60 to 60:40, and more preferably from 45:55 to 55:45.

28. The process of any one of embodiments 1 to 27, wherein (4) is conducted at a pressure in the range of from 10 to 250 bar, preferably from 20 to 200 bar, more preferably from 30 to 180 bar, more preferably from 40 to 150 bar, more preferably from 50 to 120 bar, more preferably from 60 to 100 bar, more preferably from 70 to 90 bar, and more preferably from 75 to 85 bar.

29. The process of embodiment 28, wherein the gas phase of the mixture prepared in (3) and heated in (4) comprises 50 volume-% or more of hydrogen gas, preferably 80 volume-% or more, more preferably 90 volume-% or more, more preferably 95 volume-% or more, more preferably 98 volume-% or more, more preferably 99 volume-% or more, and more preferably 99.9 volume-% or more.

30. The process of any one of embodiments 1 to 29, wherein (4) is conducted for a duration in the range of from 0.1 h to 20 h, preferably of from 0.25 h to 10 h, more preferably of from 0.5 h to 5 h, more preferably of from 1 h to 3 h, and more preferably of from 1.5 h to 2.5 h.

31. The process of any one of embodiments 1 to 30, wherein for providing the hydrogenation catalyst precursor in (1), the process comprises:
   (i) providing an aqueous solution comprising one or more salts of one or more transition metals;
   (ii) providing an aqueous solution comprising one or more bases;
   (iii) providing an aqueous dispersion comprising one or more refractory metal oxides in water;

(iv) adding the aqueous solution provided in (i) and the aqueous solution provided in (ii) to the aqueous dispersion provided in (iii) for precipitating a hydrogenation catalyst precursor;
   (v) isolating the hydrogenation catalyst precursor obtained in (iv); and
   (vi) optionally washing and/or drying and/or calcining the hydrogenation catalyst precursor isolated in (v).

32. The process of any one of embodiments 1 to 31, wherein for providing the hydrogenation catalyst in (1), the process according to embodiment 30 further comprises:
   (vii) reducing the hydrogenation catalyst precursor obtained in (v) or (vi) in a hydrogen atmosphere for obtaining a hydrogenation catalyst.

33. The process of any one of embodiments 1 to 32, wherein for providing the hydrogenation catalyst in (1), the process according to embodiment 31 further comprises:
   (viii) passivating the hydrogenation catalyst obtained in (vii) in an atmosphere comprising air, preferably in an atmosphere consisting of air.

34. The process of any one of embodiments 31 to 33, wherein in (i) the one or more transition metals are selected from the group consisting of Ni, Rh, Ir, Ru, Pt, Pd, and combinations of two or more thereof, preferably from the group consisting of Ni, Pt, Pd and combinations of two or more thereof, wherein more preferably the one or more transition metals comprise Ni and/or Pt, preferably Ni, wherein more preferably the one or more transition metals are Ni and/or Pt, preferably Ni.

35. The process of any one of embodiments 31 to 34, wherein in (ii) the one or more bases comprise one or more compounds selected from the group consisting of inorganic and organic bases, preferably from the group of inorganic bases, wherein preferably the one or more bases are selected from the group consisting of hydroxides, carbonates, aluminates, and mixtures of two or more thereof, more preferably from the group consisting of alkali metal hydroxides, alkali metal carbonates, alkali metal aluminates, and mixtures of two or more thereof, more preferably from the group consisting of alkali metal carbonates, alkali metal aluminates, and mixtures of two or more thereof, wherein more preferably the one or more bases comprise one or more alkali metal carbonates, wherein the alkali metal is preferably selected from the group consisting of Li, Na, K, Rb, Cs, and mixtures of two or more thereof, more preferably from the group consisting of Li, Na, K, and mixtures of two or more thereof, wherein more preferably the alkali metal is Na and/or K, preferably Na.

36. The process of any one of embodiments 31 to 35, wherein in (iii) the one or more refractory metal oxides are selected from the group consisting of silica, alumina, magnesia, and mixtures of two or more thereof, wherein preferably the one or more refractory metal oxides comprise silica and/or alumina, preferably silica or silica and alumina, and more preferably silica, wherein more preferably the one or more refractory metal oxides consist of silica and/or alumina, preferably of silica or of silica and alumina, and more preferably of silica.

37. The process of any one of embodiments 31 to 36, wherein in (iii) the one or more refractory metal oxides have a pore volume in the range of from 0.3 to 5 ml/g, more preferably of from 0.5 to 4 ml/g, more preferably of from 0.8 to 3.5 ml/g, more preferably of from 1 to 3 ml/g, more preferably of from 1.3 to 2.5 ml/g, more preferably of from 1.5 to 2 ml/g, more preferably of from 1.6 to 1.8 ml/g, and more preferably of from 1.7 to 1.75 ml/g, wherein the pore volume is preferably determined according to ISO 15901-3: 2007.

38. The process of any one of embodiments 31 to 37, wherein in (iv) the addition of the aqueous solution provided in (i) and the aqueous solution provided in (ii) to the aqueous dispersion provided in (iii) is conducted subsequently or simultaneously, preferably simultaneously.

39. The process of any one of embodiments 31 to 38, wherein (iv) is conducted at a temperature in the range of from 25 to 95° C., preferably of from 30 to 90° C., more preferably of from 35 to 85° C., more preferably of from 40 to 80° C., more preferably of from 45 to 75° C., more preferably of from 50 to 70° C., and more preferably of from 55 to 65° C.

40. The process of any one of embodiments 31 to 39, wherein in (iv) the pH is maintained in the range of from 5 to 10 during the precipitation of the mixed oxide, preferably of from 5.5 to 9.5, more preferably of from 6 to 9, more preferably of from 6.5 to 8.5, and more preferably of from 7 to 8.

41. The process of any one of embodiments 32 to 40, wherein reduction in (vii) is conducted at a temperature in the range of from 200 to 500° C., more preferably from 300 to 470° C., more preferably from 350 to 450° C., more preferably from 400 to 440° C., and more preferably from 420 to 430° C.

42. The process of any one of embodiments 32 to 41, wherein reduction in (vii) is conducted for a duration in the range of from 0.25 to 5 h, preferably from 0.5 to 4 h, more preferably from 1 to 3.5 h, more preferably from 1.25 to 3 h, more preferably from 1.5 to 2.5 h, and more preferably from 1.75 to 2.25 h.

43. The process of any one of embodiments 33 to 42, wherein passivation in (viii) is conducted at a temperature in the range of from 75 to 150° C., preferably from 80 to 130° C., more preferably from 85 to 120° C., more preferably from 90 to 110° C., and more preferably from 95 to 105° C.

44. The process of any one of embodiments 33 to 43, wherein passivation in (viii) is conducted for a duration in the range of from 0.25 to 4 h, preferably from 0.5 to 3 h, more preferably from 0.75 to 2.5 h, more preferably from 1 to 2 h, and more preferably from 1.25 to 1.75 h.

45. The process of any one of embodiments 1 to 30, wherein for providing the hydrogenation catalyst precursor in (1), the process comprises:
(i) providing an aqueous solution comprising one or more salts of one or more transition metals;
(ii) providing an aqueous solution comprising one or more precursor salts of silica;
(iii) providing an aqueous solution comprising one or more precursor salts of alumina;
(iv) adding the aqueous solution provided in (i) and the aqueous solution provided in (ii) to the aqueous solution provided in (iii) for precipitating a hydrogenation catalyst precursor;
(v) isolating the hydrogenation catalyst precursor obtained in (iv);
(vi) optionally washing and/or drying and/or calcining the hydrogenation catalyst precursor isolated in (v).

46. The process of any one of embodiments 1 to 30, wherein for providing the hydrogenation catalyst in (1), the process according to embodiment 45 further comprises:
(vii) reducing the hydrogenation catalyst precursor obtained in (v) or (vi) in a hydrogen atmosphere for obtaining a hydrogenation catalyst.

47. The process of any one of embodiments 1 to 30, wherein for providing the hydrogenation catalyst in (1), the process according to embodiment 46 further comprises:
(viii) passivating the hydrogenation catalyst obtained in (vii) in an atmosphere comprising air, preferably in an atmosphere consisting of air.

48. The process of any one of embodiments 45 to 47, wherein in (i) the one or more transition metals are selected from the group consisting of Ni, Rh, Ir, Ru, Pt, Pd, and combinations of two or more thereof, preferably from the group consisting of Ni, Pt, Pd and combinations of two or more thereof, wherein more preferably the one or more transition metals comprise Ni and/or Pt, preferably Ni, wherein more preferably the one or more transition metals are Ni and/or Pt, preferably Ni.

49. The process of any one of embodiments 45 to 48, wherein in (iv) the addition of the aqueous solution provided in (i) and the aqueous solution provided in (ii) to the aqueous solution provided in (iii) is conducted subsequently or simultaneously, preferably simultaneously.

50. The process of any one of embodiments 45 to 49, wherein (iv) is conducted at a temperature in the range of from 35 to 100° C., preferably from 50 to 99° C., more preferably from 70 to 98° C., more preferably from 80 to 97° C., more preferably from 85 to 96° C., and more preferably from 90 to 95° C.

51. The process of any one of embodiments 45 to 50, wherein in (iv) the pH is maintained in the range of from 6 to 10 during the precipitation of the mixed oxide, preferably of from 6.5 to 9.5, more preferably of from 7 to 9, and more preferably of from 7.5 to 8.5.

52. The process of any one of embodiments 45 to 51, wherein calcining in (vi) is conducted at a temperature in the range of from 200 to 700° C., preferably from 250 to 600° C., more preferably from 300 to 500° C., more preferably from 325 to 450° C., and more preferably from 350 to 400° C.

53. The process of any one of embodiments 45 to 52, wherein reduction in (vii) is conducted at a temperature in the range of from 200 to 500° C., preferably from 300 to 470° C., more preferably from 350 to 450° C., more preferably from 400 to 440° C., and more preferably from 420 to 430° C.

54. The process of any one of embodiments 46 to 53, wherein reduction in (vii) is conducted for a duration in the range of from 0.25 to 5 h, preferably from 0.5 to 4 h, more preferably from 1 to 3.5 h, more preferably from 1.25 to 3 h, more preferably from 1.5 to 2.5 h, and more preferably from 1.75 to 2.25 h.

55. The process of any one of embodiments 47 to 54, wherein passivation in (viii) is conducted at a temperature in the range of from 75 to 150° C., preferably from 80 to 130° C., more preferably from 85 to 120° C., more preferably from 90 to 110° C., and more preferably from 95 to 105° C.

56. The process of any one of embodiments 47 to 55, wherein passivation in (viii) is conducted for a duration in the range of from 0.25 to 4 h, preferably from 0.5 to 3 h, more preferably from 0.75 to 2.5 h, more preferably from 1 to 2 h, and more preferably from 1.25 to 1.75 h.

57. The process of any one of embodiments 1 to 56, wherein the granular material is in the form of pastilles, flakes or droplets.

58. The process of any one of embodiments 1 to 57, wherein the granular materials displays an average particle size in the range of from 1 to 25 mm, preferably from 2 to 15 mm, more preferably from 3 to 10 mm, more preferably from 4 to 8 mm, and more preferably from 5 to 6 mm.

EXPERIMENTAL SECTION

Reference Example 1: Preparation of a Nickel Containing Hydrogenation Catalyst A nickel catalyst was prepared according to Example 2 of WO 2015/008247 A2 with slight modifications. Solutions containing nickel and alumina salts, silicate, and sodium carbonate were mixed in a well stirred precipitation vessel at a temperature of 90° C. The pH of the slurry formed was about 7.5 and after 1 hour the precipitation was completed. After washing the precipitate, the precursor of the catalyst was filtered and dried in an oven at 110° C. The dried solid material was then activated with hydrogen at 425° C. for two hours and subsequently passivated in the presence of air at 100° C.

Reference Example 2: Preparation of Catalyst Droplets Comprising a Nickel Containing Hydrogenation Catalyst Catalyst droplets were prepared according to Example 1 of WO 2004/035204 A1, except that hydrogenated palm oil was employed instead of hardened soybean fat. The final catalyst droplets contained about 20 weight-% of Ni calculated as the element, wherein the droplets displayed an average particle size of 6 mm.

Reference Example 3: Preparation of Catalyst Droplets Comprising Nickel Supported on Silica as Hydrogenation Catalyst Nickel supported on silica as hydrogenation catalyst was prepared according to Example 3 of U.S. Pat. No. 9,045,410 B2. As for Reference Example 2, the resulting catalyst was then coated with hydrogenated palm oil in accordance with the procedure described in Example 1 of WO 2004/035204 A1 for affording catalyst droplets containing about 11 weight-% of Ni calculated as the element, wherein the droplets displayed an average particle size of 5 to 6 mm.

Reference Example 4: Deoxygenation of Catalyst Droplets

Figure 1:
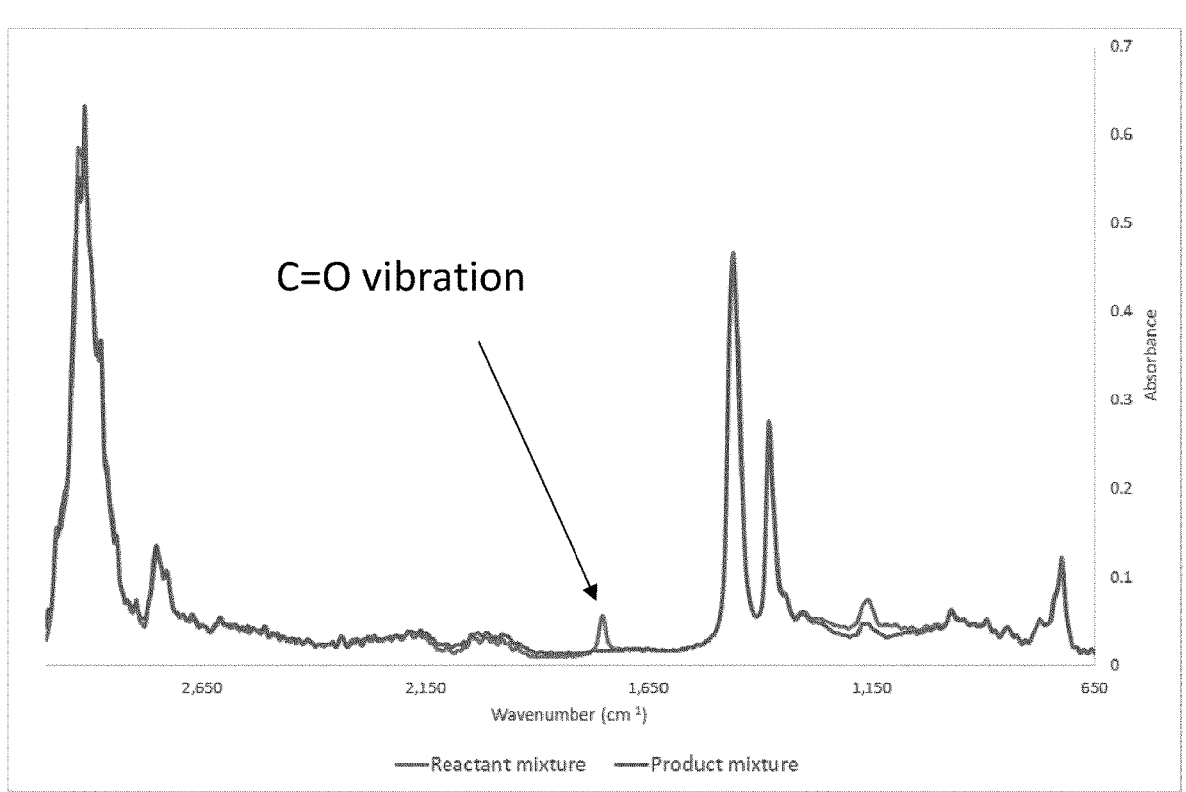
FIG. 1 displays the IR-spectrum of the mixture of Reference Example 4 prior to and after the hydrogenation treatment.
Figure 2:
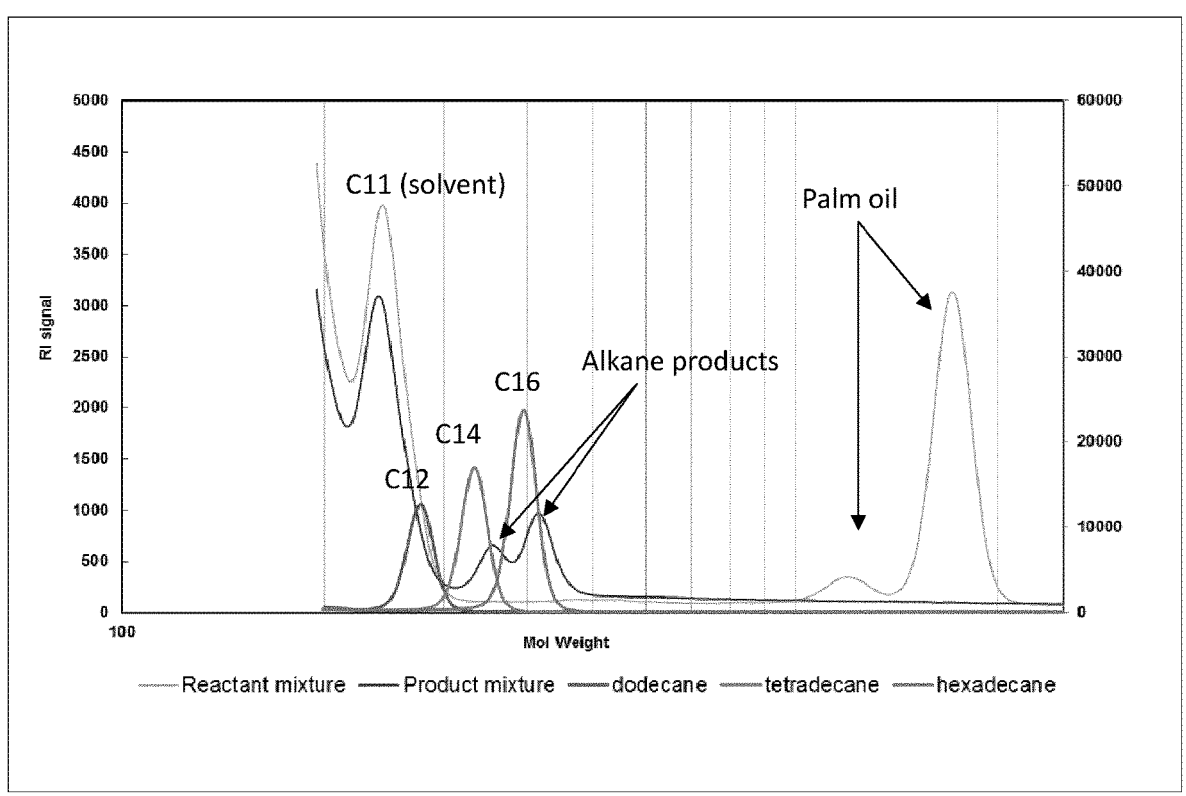
FIG. 2 displays the HPLC analysis of the composition of the mixture of Reference Example 4 prior to and after hydrogenation treatment.

The nickel catalyst of Reference Example 1 was admixed with hardened palm oil and a C9-C11 hydrocarbon solvent, and the resulting mixture was subject to hydrogenation conditions (260-280° C. and 80 bar $H_2$). As may be taken from FIG. 1 which displays the IR-spectrum of the mixture prior to and after the hydrogenation treatment, the C=O vibration at 1749 $cm^{-1}$ from the ester moieties of the hardened palm oil in the mixture prior to hydrogenation is entirely missing from the IR-spectrum taken after hydrogenation. Furthermore, as may be taken from analysis of the composition of the mixture prior to and after hydrogenation treatment by HPLC shown in FIG. 2, the C16 and C18 alkyl chains of the hardened palm oil were fully transformed to C15 and C17 alkanes. To this effect, dodecane, tetradecane and hexadecane were injected into the HPLC as reference compounds. Thus, the results in FIGS. 1 and 2 show that the hydrogenation treatment led to the deoxygenation of the hardened palm oil, to the effect that the oil was converted to hydrocarbons either by decarbonylation and/or decarboxylation of the fatty acid moieties. As a result, it has surprisingly been found that a hydrogenation catalyst for the hydrogenation of hydrocarbon feedstocks may be effectively protected by coating thereof with one or more organic compounds containing one or more carboxylic acid and/or one or more ester moieties, wherein said compounds are deoxygenated in situ under the conditions for the hydrogenation of hydrocarbon feedstocks, as a result of which they are transformed to water, CO, and/or $CO_2$ and hydrocarbons. As a result, it has quite unexpectedly been found that the protective coating does not contaminate the hydrocarbon feedstock but rather affords hydrocarbons which may easily be separated from the hydrogenated hydrocarbon product by distillation or the like.

Example 1: Hydrogenation of a Hydrocarbon Feedstock

Resin hydrogenation tests were performed in a batch type reactor HP-9 using high Sulphur C9-resin feed 4 (125 ppm). The conditions for a standard test were:
    agitation: 1100 rpm;
    pressure: 80 bar;
    temperature: 270° C.;
    feed: 75 g resin/75 g Exxsol D40 (ExxonMobil);
    runtime: 2 hours;
    catalyst loading: Reference Example 1: 0.75 g; Reference Example 2: 2.5 g; Reference Example 3: 4.5 g; wherein the amount of droplets was chosen such that the nickel loading was the same in each of the samples.

The hydrogenation activity was calculated using linear regression between 0-30% and/or 30-70% activity. UV activity is calculated from the decrease of UV peak height (measured at 274 nm) relative to the non-hydrogenated resin. The hydrocracking activity of a sample is expressed as the shift of the molecular weight distribution curve toward a lower molecular weight after 2 hours of hydrogenation. Two methods were used to express the cracking:

Calculated from the shift of the peak maximum, according to $dMp=(Mp_{feed}-Mp_{product})/Mp_{feed}\times100\%$;

Calculated from the decrease of molecular weight fraction above 5000 g/mol relative to the feed according to $dHv=(weight{<}5000_{feed}-weight{<}5000_{product})/weight{<}5000_{feed}\times100\%$.

| | Activity (%) | UV arom (% conv.) | Color | dMp (%) | dHeavies (%) |
|---|---|---|---|---|---|
| Ref. Ex. 1 (comparative) | 100 | 93 | 7 | 5 | 32 |
| Ref. Ex. 2 (inventive) | 89 | 89 | 12 | −11 | 12 |
| Ref. Ex. 3 (inventive) | 153 | 94 | 15 | −11 | 1 |

Thus, as may be taken from the results obtained for hydrogenation employing the catalyst from reference example 2, its performance is comparable to the catalyst from a reference example 1, this showing that protection of the catalyst by coating with the hydrogenated palm oil did not lead to a substantial decrease in catalyst activity. Reference example 3, on the other hand, which comprises nickel supported on silica as the hydrogenation catalyst displayed a superior hydrogenation activity compared to the uncoated catalyst of reference example 1.

CITED PRIOR ART REFERENCES

WO 2015/008247 A2
WO 2017/208164 A1
WO 2004/035204 A1
U.S. Pat. No. 9,045,410 B2
US 2008/161588 A1
US 2005/027136 A1
US 2014/336287 A1

We claim:

1. A process for the hydrogenation of an unsaturated hydrocarbon feedstock comprising:
   (1) preparing a granular material having particles, wherein the particles of the granular material comprise a hydrogenation catalyst, or a precursor thereof, and one or more organic compounds, wherein the one or more organic compounds comprise one or more carboxylic acid and/or one or more ester and/or one or more ether moieties and wherein the one or more organic compounds have a melting point in a range from 30° C. to 100° C.;
   (2) providing an unsaturated hydrocarbon feedstock;
   (3) preparing a mixture comprising the granular material obtained in (1), the unsaturated hydrocarbon feedstock provided in (2), hydrogen gas, and optionally a solvent system; and
   (4) heating the mixture prepared in (3) to a temperature in the range of from 210 to 360° C. for hydrogenating the hydrocarbon feedstock.

2. The process of claim 1, wherein for preparing the granular material in (1), the process comprises:
   (1.a) providing a hydrogenation catalyst;
   (1.b) providing one or more organic compounds comprising one or more carboxylic acid and/or one or more ester and/or one or more ether moieties;
   (1.c) optionally heating the one or more organic compounds provided in (1.b) to a temperature above the melting point of the one or more organic compounds;
   (1.d) dispersing the hydrogenation catalyst provided in (1.a) in the one or more organic compounds provided in (1.b) and optionally heated in (1.c);
   (1.e) shaping the dispersion obtained in (1.d);
   (1.f.) cooling the dispersion obtained in (1.e) to a temperature below the melting point of the one or more organic compounds.

3. The process of claim 1, wherein in (1) the one or more organic compounds comprise one or more compounds selected from the group consisting of triglycerides, fatty acids, and mixtures of two or more thereof.

4. The process of claim 1, wherein the unsaturated hydrocarbon feedstock comprises one or more alkanes.

5. The process of claim 1, wherein the unsaturated hydrocarbon feedstock comprises one or more compounds selected from the group consisting of C5 resins, C9 resins, C5/C9 copolymer resins, dicyclopentadiene resins, and mixtures of two or more thereof.

6. The process of claim 1, wherein the solvent system comprises one or more hydrocarbons.

7. The process of claim 1, wherein the weight ratio of the hydrogenation catalyst to the one or more organic compounds in the particles of the granular material in (1) is in the range of from 5:95 to 75:25.

8. The process of claim 1, wherein the hydrogenation catalyst in (1) comprises one or more transition metals selected from the group consisting of Ni, Rh, Ir, Ru, Pt, Pd, and combinations of two or more thereof.

9. The process of claim 8, wherein the amount of the one or more transition metals in the hydrogenation catalyst is in the range of from 5 to 95 weight-% calculated as the element and based on 100 weight-% of the hydrogenation catalyst.

10. The process of claim 8, wherein the one or more transition metals are present in the elemental form in an amount of 50 weight-% or more based on 100 weight-% of the one or more transition metals calculated as the element.

11. The process of claim 1, wherein a pore volume of the hydrogenation catalyst in (1) is in the range of from 0.1 to 1.5 ml/g, wherein the pore volume refers to the hydrogenation catalyst devoid of any compounds in its pores.

12. The process of claim 1, wherein the weight ratio of the granular material to the unsaturated hydrocarbon feedstock in the mixture in (3) is in the range of from 1:99 to 40:60.

13. The process of claim 1, wherein the weight ratio of the unsaturated hydrocarbon feedstock to the solvent system in the mixture in (3) is in the range of from 5:95 to 95:5.

14. The process of claim 1, wherein for providing the hydrogenation catalyst in (1), the process comprises:
   (i) providing an aqueous solution comprising one or more salts of one or more transition metals;
   (ii) providing an aqueous solution comprising one or more bases;
   (iii) providing an aqueous dispersion comprising one or more refractory metal oxides in water;
   (iv) adding the aqueous solution provided in (i) and the aqueous solution provided in (ii) to the aqueous dispersion provided in (iii) for precipitating an oxide of the one or more transition metals;
   (v) isolating the oxide obtained in (iv);
   (vi) optionally washing and/or drying and/or calcining the oxide isolated in (v);
   (vii) reducing the oxide obtained in (v) or (vi) in a hydrogen atmosphere.

15. The process of claim 1, wherein for providing the hydrogenation catalyst in (1), the process comprises:
   (i) providing an aqueous solution comprising one or more salts of one or more transition metals;
   (ii) providing an aqueous solution comprising one or more precursor salts of silica;
   (iii) providing an aqueous solution comprising one or more precursor salts of alumina;

(iv) adding the aqueous solution provided in (i) and the aqueous solution provided in (ii) to the aqueous solution provided in (iii) for precipitating a mixed oxide;

(v) isolating the mixed oxide obtained in (iv);

optionally washing and/or drying and/or calcining the mixed oxide isolated (vi) in (v);

(vii) reducing the mixed oxide obtained in (v) or (vi) in a hydrogen atmosphere.

* * * * *